US009815063B2

(12) United States Patent
Carney (10) Patent No.: US 9,815,063 B2
(45) Date of Patent: Nov. 14, 2017

(54) RADIONUCLIDE ASSAY STATION

(71) Applicant: Siemens Medical Solutions USA, Inc., Malvern, PA (US)

(72) Inventor: Leon Carney, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 146 days.

(21) Appl. No.: 14/920,624

(22) Filed: Oct. 22, 2015

(65) Prior Publication Data

US 2016/0114328 A1   Apr. 28, 2016

Related U.S. Application Data

(60) Provisional application No. 62/067,088, filed on Oct. 22, 2014.

(51) Int. Cl.
| | |
|---|---|
| *G01N 35/10* | (2006.01) |
| *B01L 9/06* | (2006.01) |
| *G01N 1/28* | (2006.01) |
| *G01N 35/04* | (2006.01) |

(52) U.S. Cl.
CPC ............ *B01L 9/06* (2013.01); *G01N 1/28* (2013.01); *B01L 2200/18* (2013.01); *G01N 2035/041* (2013.01); *G01N 2035/0406* (2013.01); *G01N 2035/0477* (2013.01); *G01N 2035/0479* (2013.01); *G01N 2035/0481* (2013.01)

(58) Field of Classification Search
CPC . B01L 9/06; B01L 2200/18; G01N 2001/002; G01N 1/00; G01N 35/10; G01N 2035/041; G01N 2035/0477; G01N 2035/0479; G01N 2035/0481; B25J 21/00; B25J 9/123; F15B 2215/30; F15B 15/00; G21C 19/12; G01T 7/08
USPC ....................................... 73/864.91
See application file for complete search history.

(56) References Cited

U.S. PATENT DOCUMENTS

| | | | | |
|---|---|---|---|---|
| 3,830,628 | A |  | 8/1974 | Kaartinen |
| 4,144,461 | A | * | 3/1979 | Glasser ................ G21F 5/015 250/395 |
| 4,506,155 | A | * | 3/1985 | Suzuki ................. G21F 5/015 250/252.1 |
| 5,267,478 | A | * | 12/1993 | Stridsberg ............ B23Q 5/385 318/593 |

(Continued)

*Primary Examiner* — Peter Macchiarolo
*Assistant Examiner* — Alexander Mercado (57) ABSTRACT

An improved dose assay station for preparing unit-dose samples of radionuclide from a multi-dose vial is disclosed. The improved assay station is provided an assay chamber and a radionuclide sample lifter provided within the assay chamber. The radionuclide sample lifter is configured for lowering a radionuclide sample container into the assay chamber and raising the radionuclide sample container out of the assay chamber. The radionuclide sample lifter includes a magnetically coupled pneumatic actuator; and a carriage attached to the magnetically coupled pneumatic actuator, the carriage being configured for holding the radionuclide sample container, wherein the magnetically coupled pneumatic actuator moves the carriage between a first position and a second position within the assay chamber, wherein the first position places the carriage near the top end of the assay chamber and the second position places the carriage near the bottom end of the assay chamber.

10 Claims, 7 Drawing Sheets

(56) References Cited

U.S. PATENT DOCUMENTS

| | | | | | |
|---|---|---|---|---|---|
| 5,309,959 | A | * | 5/1994 | Shaw | B65B 3/003 141/103 |
| 5,442,892 | A | * | 8/1995 | Burns, III | B65B 69/00 53/453 |
| 5,479,969 | A | | 1/1996 | Hardie et al. | |
| 5,844,340 | A | * | 12/1998 | Noda | F15B 15/086 310/103 |
| 5,948,360 | A | * | 9/1999 | Rao | G01N 30/24 422/63 |
| 5,993,744 | A | * | 11/1999 | Rao | G01N 30/24 422/539 |
| 6,279,295 | B1 | * | 8/2001 | Girard | B65B 11/02 53/389.3 |
| 8,069,886 | B1 | * | 12/2011 | Yanke | A61J 1/20 141/252 |
| 2003/0004463 | A1 | * | 1/2003 | Reilly | A61K 51/1282 604/124 |
| 2003/0089581 | A1 | * | 5/2003 | Thompson | B65G 23/18 198/619 |
| 2005/0029465 | A1 | * | 2/2005 | Lemer | G01T 1/167 250/374 |
| 2005/0278066 | A1 | * | 12/2005 | Graves | G21F 5/015 700/239 |
| 2007/0235641 | A1 | * | 10/2007 | Allberg | A61N 5/1075 250/252.1 |
| 2008/0166292 | A1 | * | 7/2008 | Levin | A61M 5/1723 424/1.11 |
| 2009/0194677 | A1 | * | 8/2009 | Allberg | G01T 1/20 250/252.1 |
| 2009/0283668 | A1 | * | 11/2009 | Gilbertson | A61B 6/037 250/252.1 |
| 2013/0020175 | A1 | * | 1/2013 | McKeen | G01N 1/31 198/346.1 |
| 2013/0130369 | A1 | * | 5/2013 | Wilson | B01L 3/5085 435/289.1 |
| 2013/0192391 | A1 | * | 8/2013 | Bruehwiler | G01N 1/08 73/863.01 |
| 2015/0276580 | A1 | * | 10/2015 | Fukuju | G01N 21/13 436/501 |

* cited by examiner

FIG. 7

RADIONUCLIDE ASSAY STATION

CROSS-REFERENCE TO RELATED APPLICATION

This application claims priority under 35 U.S.C. §119(e) from co-pending U.S. Provisional Application Ser. No. 62/067,088, filed Oct. 22, 2014, the entirety of which is hereby incorporated by reference herein.

FIELD

The present disclosure relates in general to the preparation and handling of radionuclide unit-dose samples that are used in positron emission tomography (PET).

BACKGROUND

During the preparation of unit-dose samples of radionuclides from a multi-dose vial of a PET drug, it is necessary to repeatedly place samples into a dose assay chamber for dose calibration and then subsequently remove the samples from the chamber. This process must be performed quickly and precisely while simultaneously protecting personnel and maintaining a high-quality air environment to prevent microbial contamination of the samples.

Existing technology requires either a manual placement of the samples or use of a pneumatic remote lifting device for the samples. The manual operation requires the operator to lower the samples into the assay chamber and subsequently lift the samples out of the chamber. This process necessitates unnecessary movements that makes the operation slow and introduces an increased risk of dropping the samples during placement. The existing pneumatic remote lifting devices, while an improvement over the manual method, use compressed air to provide a cushion of air underneath a platform carrying the radionuclide sample to lift or lower the platform. The platform is directly supported by the cushion of compressed air flowing upwards against the platform and, therefore, a quantity of air is always flowing upward and past the edges of the platform mechanism. Because the radionuclide samples sitting on the topside of the platform is exposed to the compressed air flowing around it, this compromises the quality of the immediate surroundings. This introduces increased risk of microbial contamination during sample handling.

Therefore, there is a need for an improved system for handling radionuclide samples that lowers the radionuclide samples into an assay chamber and then lift them out of the assay chamber that accomplishes this remotely and without compromising the quality of the radionuclide samples' immediate surroundings.

SUMMARY

According to an aspect of the present disclosure, an improved dose assay station for preparing unit-dose samples of radionuclide from a multi-dose vial is disclosed. The improved assay station is provided an assay chamber and a radionuclide sample lifter provided within the assay chamber. The radionuclide sample lifter is configured for lowering a radionuclide sample container into the assay chamber and raising the radionuclide sample container out of the assay chamber. The radionuclide sample lifter includes a magnetically coupled pneumatic actuator; and a carriage attached to the magnetically coupled pneumatic actuator, the carriage being configured for holding the radionuclide sample container, wherein the magnetically coupled pneumatic actuator moves the carriage between a first position and a second position within the assay chamber, wherein the first position places the carriage near the top end of the assay chamber and the second position places the carriage near the bottom end of the assay chamber.

According to some embodiments, a radionuclide sample lifter configured for lowering a radionuclide sample container into an assay chamber and raising the radionuclide sample container out of the assay chamber is disclosed. The radionuclide sample lifter comprises a magnetically coupled pneumatic actuator and a carriage attached to the magnetically coupled pneumatic actuator, the carriage being configured for holding the radionuclide sample container. The magnetically coupled pneumatic actuator moves the carriage between a first position and a second position within the assay chamber, wherein the first position places the carriage near the top end of the assay chamber and the second position places the carriage near the bottom end of the assay chamber.

BRIEF DESCRIPTION OF THE DRAWINGS

All drawing figures are schematic and are not necessarily to scale.

DETAILED DESCRIPTION

This description of the exemplary embodiments is intended to be read in connection with the accompanying drawings, which are to be considered part of the entire written description.

Figure 1:
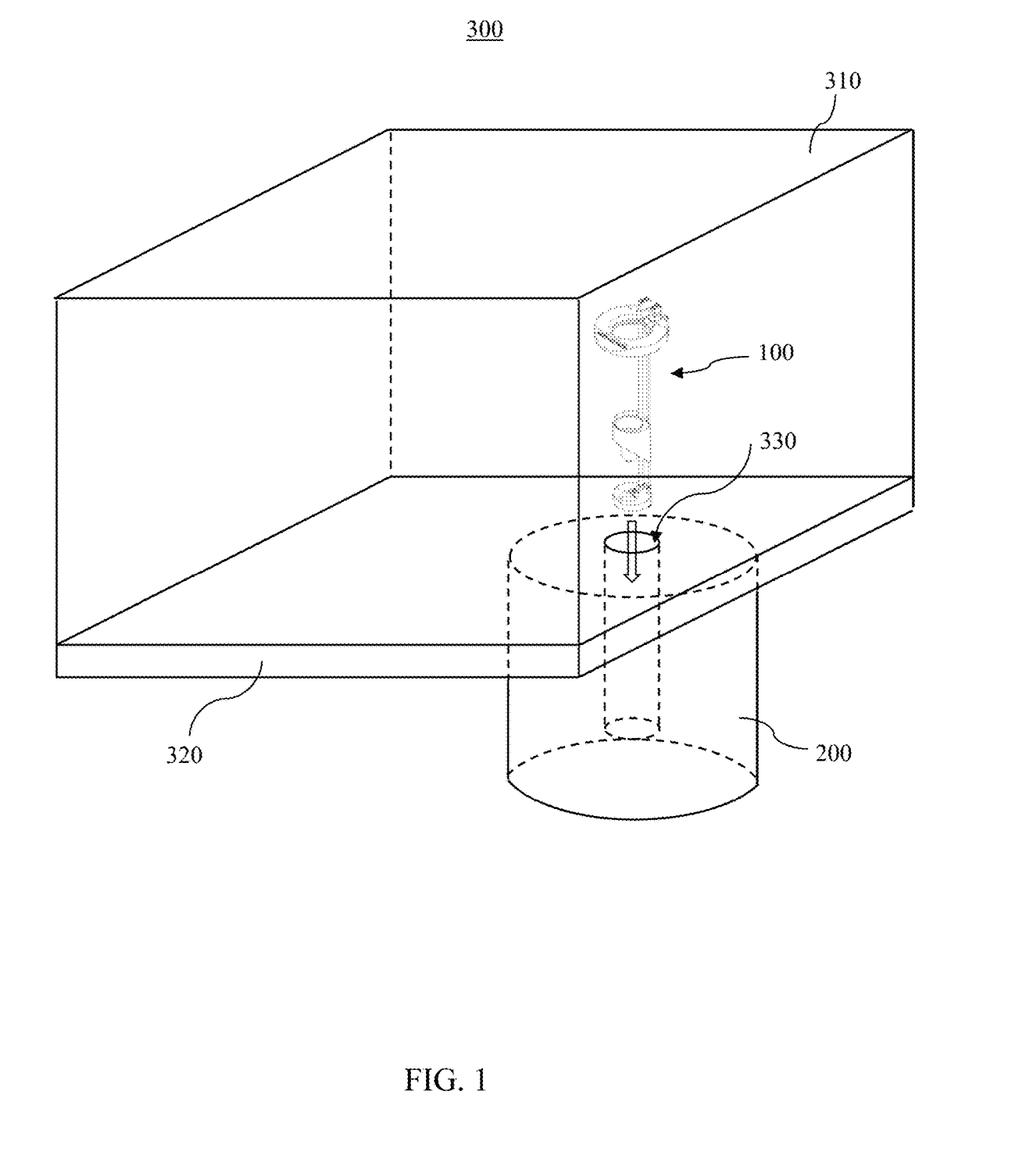
FIG. 1 shows a radionuclide dose assay station according to the present disclosure.

Referring to FIG. 1, according to an aspect of the present disclosure a radionuclide dose assay station 300 for preparing unit-dose samples of radionuclide is disclosed. The radionuclide dose assay station comprises an assay chamber 200 and a radionuclide sample lifter 100 provided within the assay chamber 200. The assay chamber 200 can be equipped with a well counter, such as those available from Capintec, Inc. The radionuclide dose assay station 300 also has an enclosure 310 that defines the hot cell within which the radionuclide material is handled. For example, dispensing of the radionuclide material from a multi-dose vial into single-dose syringes, for example, is conducted within the hot cell 310. The floor 320 of the hot cell 310 is provided with an opening 330 which provides access to the assay chamber 200. Various parts of the assay station 300 are made of lead in order to protect the users from radiation. In this illustration, the radionuclide sample lifter 100 is shown hanging above the opening 330 in an exploded view in order to show the radionuclide sample lifter 100. In normal operating condition for the radionuclide dose assay station 300, the radionuclide sample lifter 100 is lowered into the assay chamber 200 through the opening 330 and is positioned inside the assay chamber 200.

Figure 2:
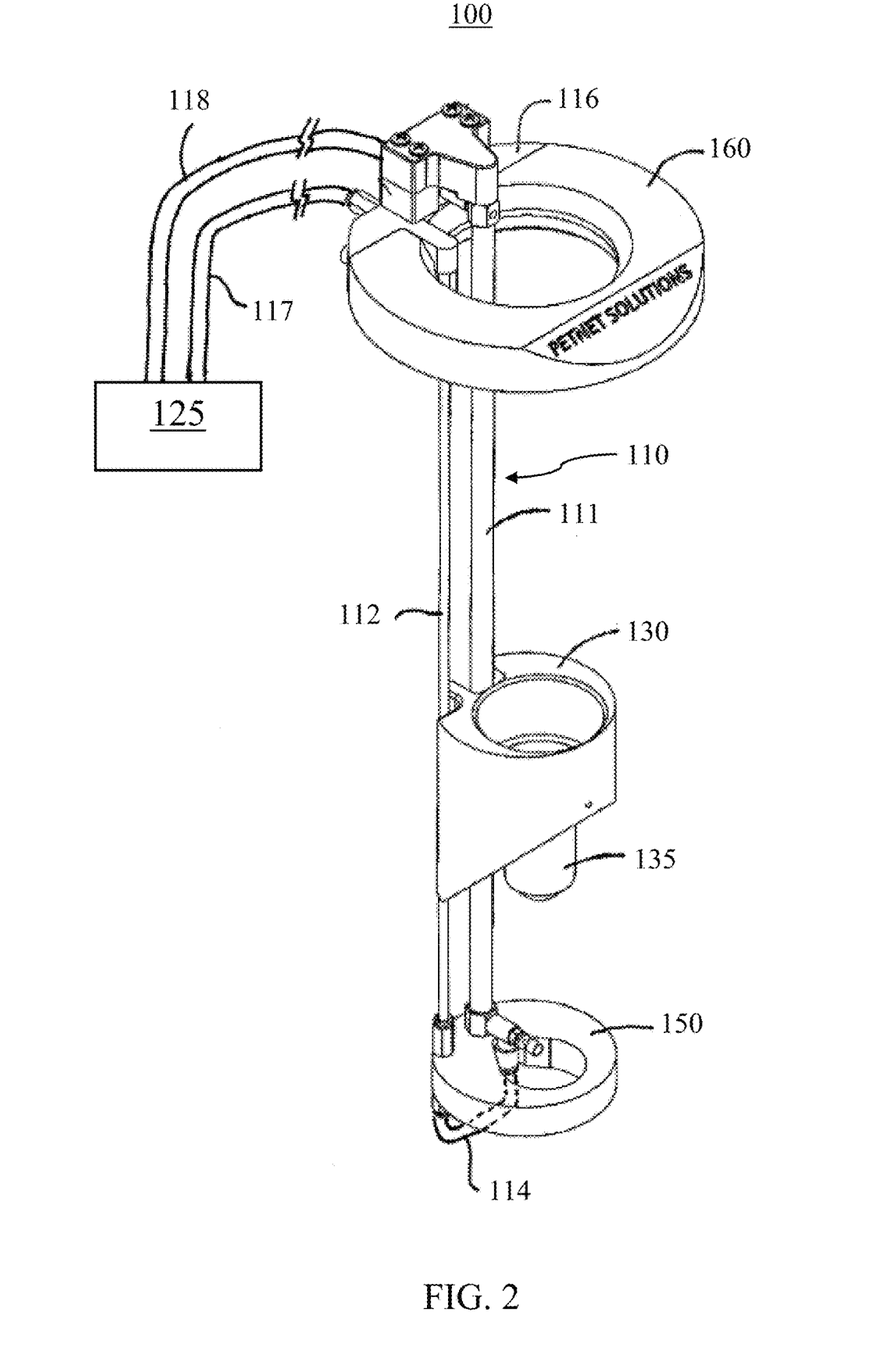
FIG. 2 shows the radionuclide sample lifter according to the present disclosure.

Referring to FIG. 2, the radionuclide sample lifter 100 is described in more detail. The radionuclide sample lifter 100 comprises a magnetically coupled pneumatic actuator 110 and a carriage 130 movably attached to the magnetically coupled pneumatic actuator 110. The carriage 130 is configured for holding the radionuclide sample container. The carriage 130 can include a sleeve 135 provided on the bottom side of the carriage 130. The sleeve 135 provides a protection for the radionuclide sample container being held by the carriage 130. The magnetically coupled pneumatic actuator 110 moves the carriage between a first position and a second position within the assay chamber 200. The first position is the fully raised position of the carriage 130 and places the carriage 130 near the top end of the assay chamber 200. The second position is the fully lowered position of the carriage 130 and places the carriage near the bottom end of the assay chamber 200. The radionuclide sample lifter 100 is provided inside the assay chamber 200 and, thus, by placing the radionuclide sample container inside the carriage 130, the radionuclide sample can be lowered into the assay chamber for measurement and then subsequently lifted out of the assay chamber.

In one embodiment, the magnetically coupled pneumatic actuator 110 comprises a stationary shaft 111 and an external magnetic slug 120 (see FIGS. 5, 6, and 7) that is configured to move linearly along the stationary shaft 111. The carriage 130 is coupled to the external magnetic slug 120 and thereby allowing the carriage 130 to be moved up and down along the stationary shaft 111.

Referring to FIG. 2, the radionuclide sample lifter 100 also comprises a second stationary shaft 112 for carrying compressed air. A bottom plate 150 provided at the bottom end of the radionuclide sample lifter 100. The magnetically coupled pneumatic actuator 110 is affixed to the bottom plate 150.

Provided at the top end of the radionuclide sample lifter 100 is an air manifold 116 that connects the stationary shaft 111 and the second stationary shaft 112 to a pneumatic control switch 125 via air supply tubes 118 and 117, respectively. The pneumatic control switch 125 delivers compressed air to the magnetically coupled pneumatic actuator 110 via the air manifold 116.

Figure 3:
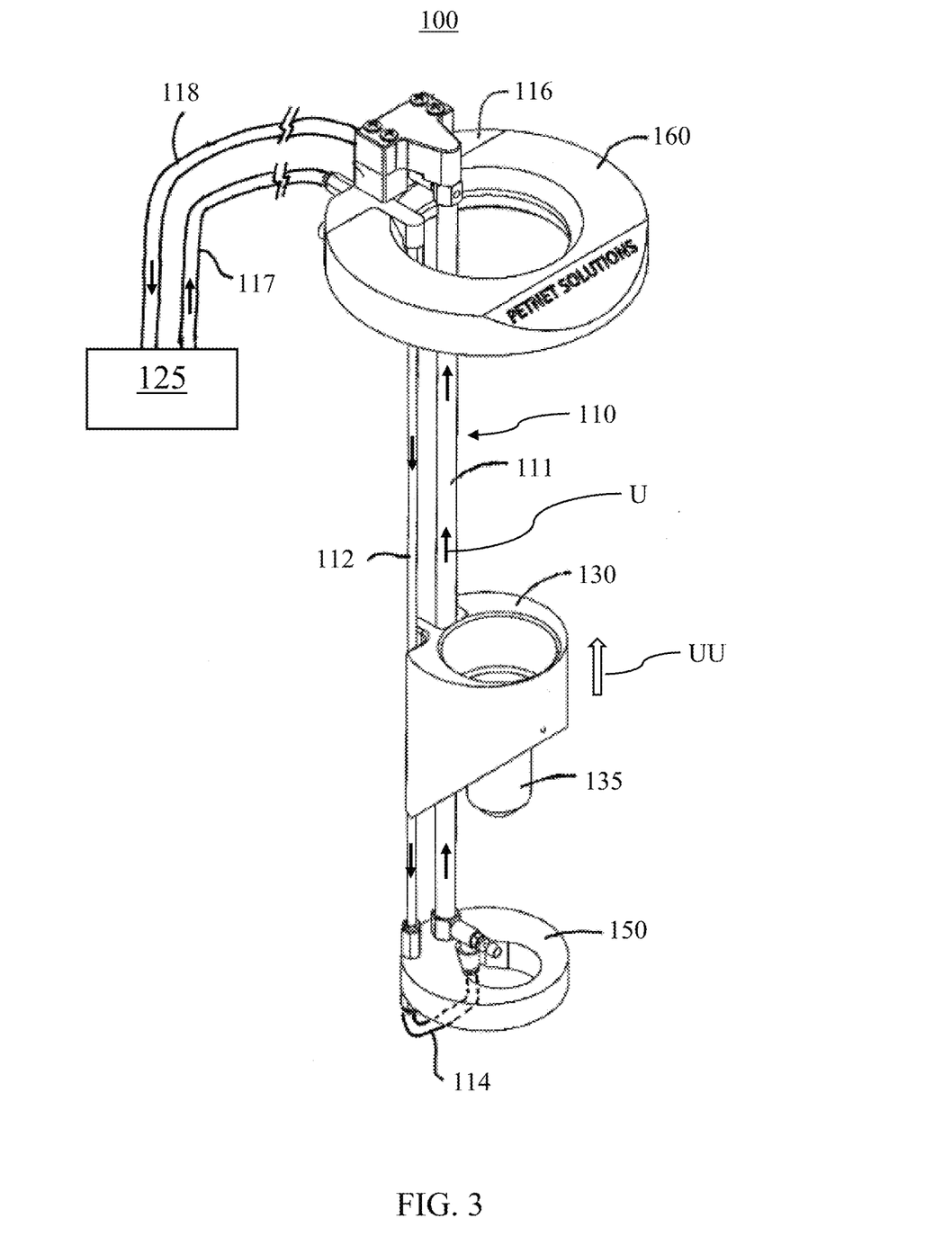
FIG. 3 shows the radionuclide sample lifter of the present disclosure in a raising mode.
Figure 4:
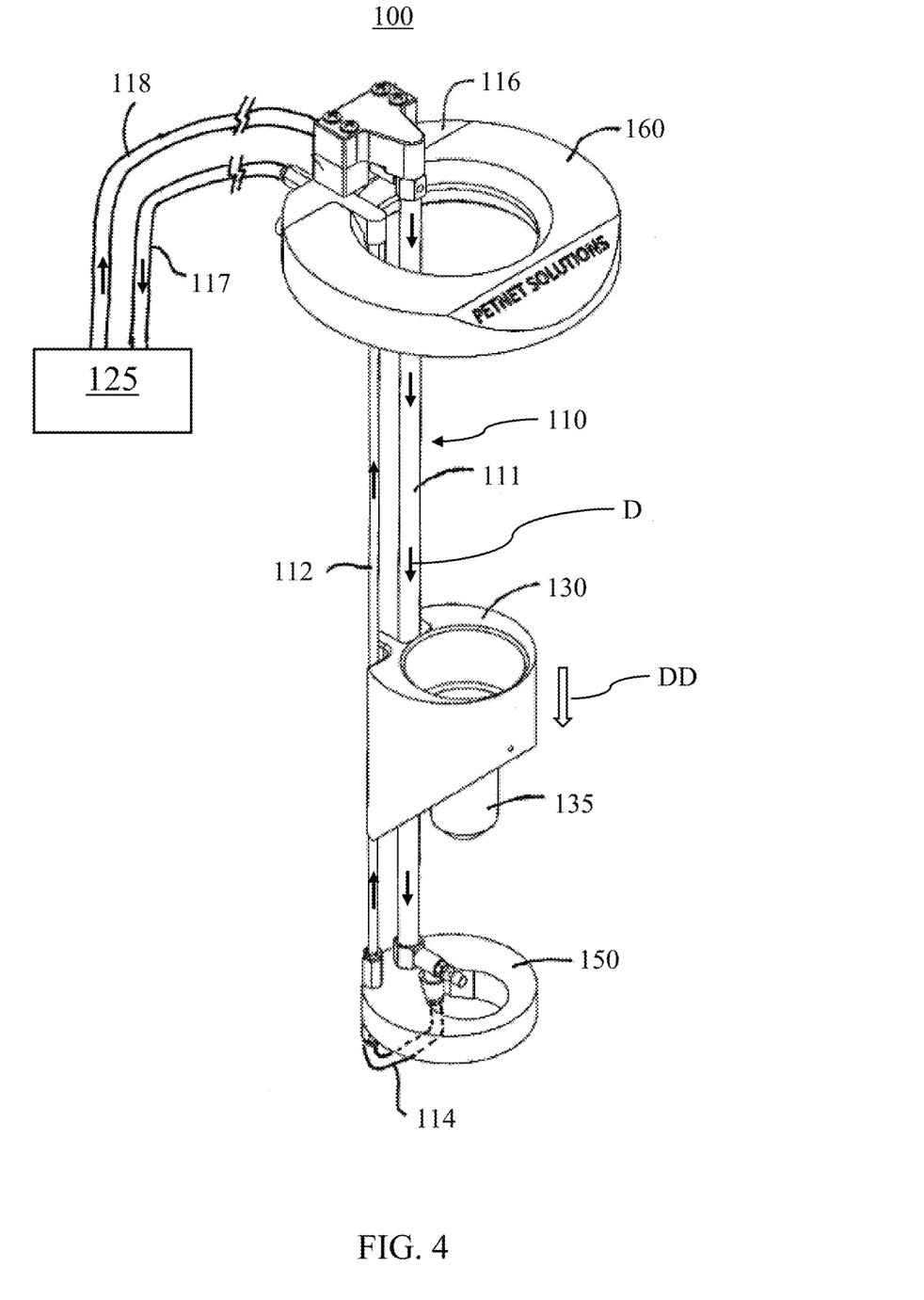
FIG. 4 shows the radionuclide sample lifter of the present disclosure in a lowering mode.

Referring to FIGS. 3 and 4, the operation of the radionuclide sample lifter 100 will be described. FIG. 3 illustrates the radionuclide sample lifter 100 in a raising mode. In the raising mode, the compressed air from the pneumatic control switch 125 is flowing via the air supply tube 117 and through the second stationary shaft 112. The second stationary shaft 112 and the stationary shaft 111 are connected via a connecting tube 114 at the bottom end so that the compressed air from the second stationary shaft 112 is delivered to the bottom end of the stationary shaft 111 and flows upward (shown by the arrow U) through the stationary shaft 111. Thus, the compressed air is confined to the sealed pneumatic system comprised of the air supply tubes 118, 117, and the stationary shaft 111, and the second stationary shaft 112. Unlike in the conventional pneumatic radionuclide sample lifters, the radionuclide sample containers placed in the carriage 130 are never directly exposed to the compressed air.

Figure 7:
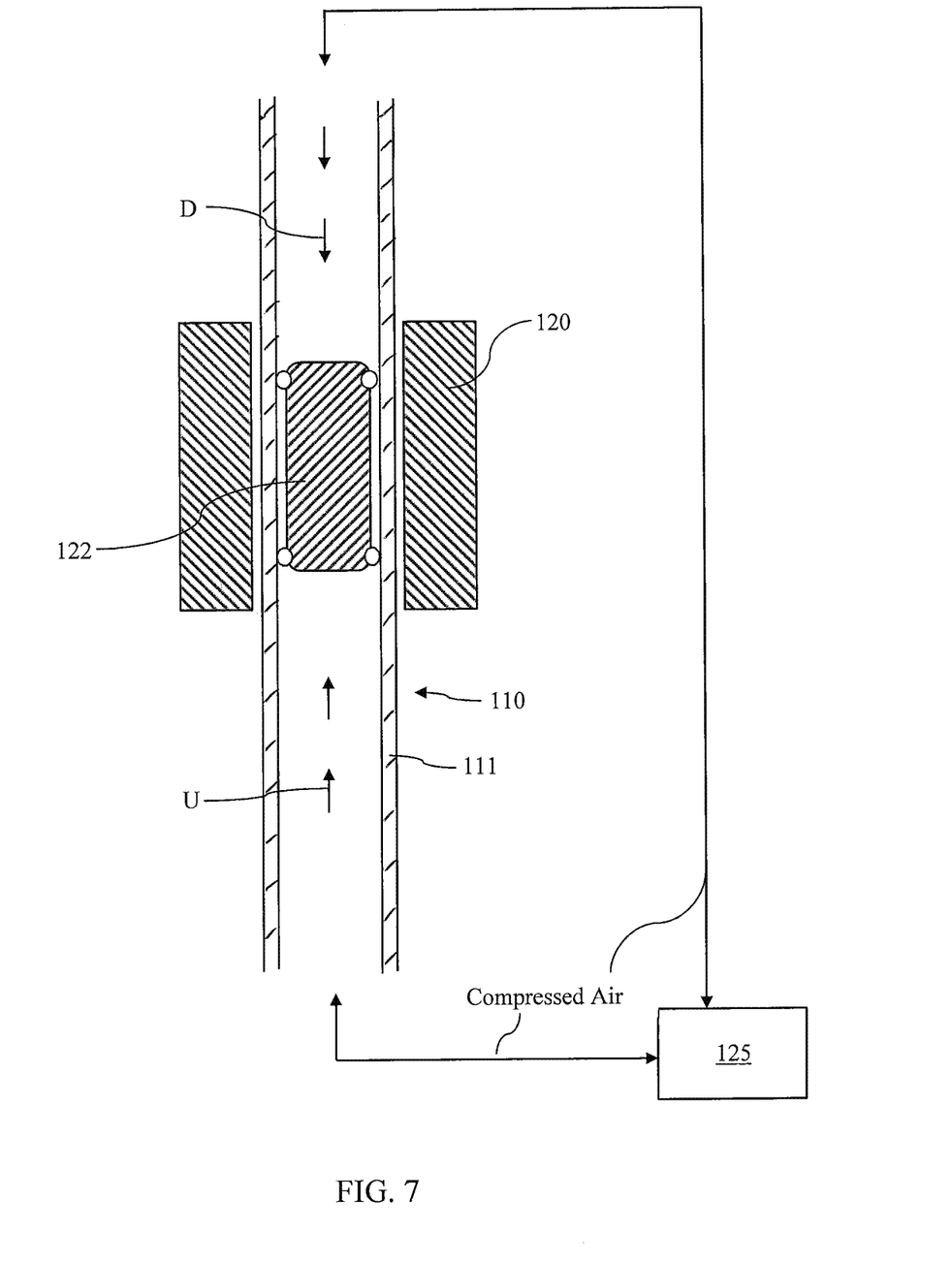
FIG. 7 is a cross-sectional view of the stationary shaft of the magnetically coupled pneumatic actuator.

Shown in FIG. 7 is a longitudinal cross-sectional view of the stationary shaft 111 illustrating how the magnetically coupled pneumatic actuator 110 operates. The magnetically coupled pneumatic actuator 110 comprises an internal magnetic slug 122 provided inside the stationary shaft. The internal magnetic slug 122 is configured move up and down within the stationary shaft 111 by the urging of the compressed air. The direction of the internal magnetic slug 122's movement is controlled according to the direction of the compressed air flow inside the stationary shaft 111.

Thus, in order to move the internal magnetic slug 122 upward, the compressed air is delivered by the pneumatic control switch 125 in a manner such that the compressed air flows upward as noted by the arrow U. On the other hand, in order to move the internal magnetic slug 122 downward, the compressed air is delivered by the pneumatic control switch 125 in a manner such that the compressed air flows downward as noted by the arrow D.

The magnetically coupled pneumatic actuator 110 is provided with an external magnetic slug 120. The external magnetic slug 120 has a bore through which the stationary shaft 111 is received. The internal magnetic slug 122 and the external magnetic slug 120 are magnetic and their magnetic polarity is oriented so that the internal magnetic slug 122 and the external magnetic slug 120 magnetically couple (i.e., they attract one another). Because of this magnetic coupling between the internal magnetic slug 122 and the external magnetic slug 120, the external magnetic slug 120 can be moved along the actuator's stationary shaft 111 by driving the internal magnetic slug 122 using the compressed air within the stationary shaft 111. Thus, as the internal magnetic slug 122 moves inside the stationary shaft 111 urged by the compressed air, the external magnetic slug 120 moves along with the internal magnetic slug 122. The carriage 130 is movably attached to the magnetically coupled pneumatic actuator 110 by being attached to the external magnetic slug 120. So, when the internal magnetic slug 122 is moved by the compressed air in the stationary shaft 111, the external magnetic slug 120, and in turn, the carriage 130 move accordingly. The magnetically coupled pneumatic actuators such as the actuator 110 is readily available in the pneumatic control industry and more detailed explanation of its components is not necessary here.

FIG. 4 illustrates the radionuclide sample lifter 100 in a lowering mode. In the lowering mode, the compressed air from the pneumatic control switch 125 is flowing via the air supply tube 118 and through the stationary shaft 111. The compressed air is moving downward, as noted by the arrow D, through the stationary shaft 111. The compressed air is moving the internal magnetic slug 122 downward, which in turn, moves the carriage 130 in downward direction DD. The compressed air then flows through the connecting tube 114, then through the second stationary shaft 112 and returns to the pneumatic control switch 125 via the tube 117.

Figure 5:
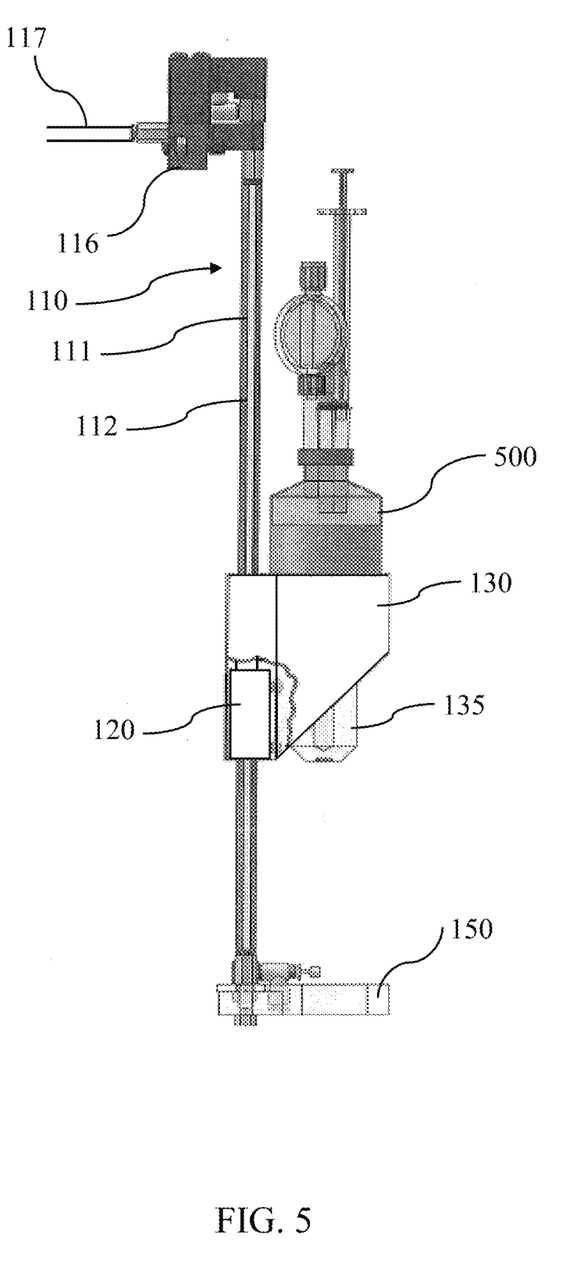
FIG. 5 is a side view of the magnetically coupled pneumatic actuator according to the present disclosure carrying a multi-dose vial in its carriage.
Figure 6:
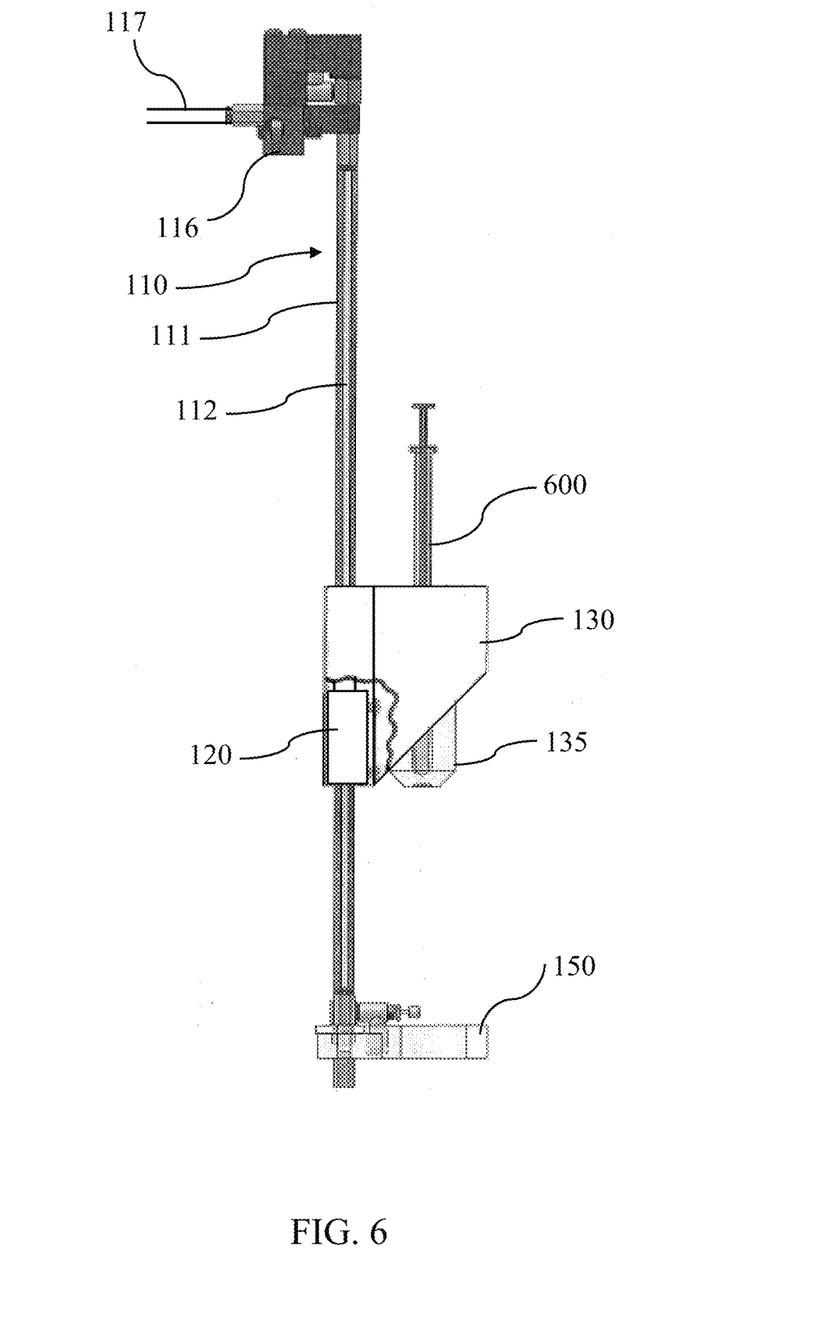
FIG. 6 is a side view of the magnetically coupled pneumatic actuator according to the present disclosure carrying a unit-dose syringe in its carriage.

FIG. 5 shows a side view of the magnetically coupled pneumatic actuator 110 that has a radionuclide sample container placed in the carriage 130. A portion of the carriage 130 has been cutaway to show the attachment of the carriage to the external magnetic slug 120. In this embodiment, the radionuclide sample container is a multi-dose vial 500. FIG. 6 is a side view of the magnetically coupled pneumatic actuator 110 where the radionuclide sample container is a unit-dose syringe 600. A portion of the carriage 130 has been cutaway in FIG. 6 also to show the attachment of the carriage to the external magnetic slug 120.

The radionuclide container can be a multi-dose vial 500 or a unit-dose syringe 600. The carriage 130 is configured to receive and hold either the multi-dose vial 500 or the unit-dose syringe 600. This is useful because during the preparation of the unit-dose sample of the radionuclide, the radionuclide material is dispensed into a unit-dose syringe 600 from a multi-dose vial 500 and it is optimal if both the multi-dose vial 500 and the unit-dose syringe 600 can be individually measured in the assay chamber. The multi-dose vial 500 can be placed in the assay chamber to measure how much radionuclide material is in the vial. Then, after a desired amount of radionuclide material is dispensed into a unit-dose syringe 600, the unit-dose syringe can be placed in the assay chamber to measure and confirm that a correct amount is in the unit-dose syringe. Each time the unit-dose syringe or the multi-dose vial is placed in the assay chamber, the radionuclide sample lifter 100 would simplify the operation and make it safer for the operator.

As described above, in the magnetically coupled pneumatic actuator 110 in the radionuclide sample lifter 100, the compressed air that provides the actuation is in a sealed system and the compressed air is not released into the assay chamber or the hot cell of the assay station. The actuation by the compressed air can be triggered by a foot pedal or other remote triggering device that are well known in the art. Thus, the radionuclide assay chamber of the present disclosure maintains efficient and precise sample handling while protecting the samples from potential microbial contamination due to a compromised clean air environment inside the hot cell. The quality of the compressed air used in the radionuclide assay chamber of the present disclosure is not an issue because the system does not release the compressed air into the controlled environment of the assay station.

The radionuclide sample assay chamber of the present disclosure is not limited to the specific embodiments described herein. The above description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A radionuclide dose assay station for preparing unit-dose samples of radionuclide from a multi-dose vial comprising:
   an assay chamber; and
   a radionuclide sample lifter provided within the assay chamber, the radionuclide sample lifter configured for lowering a radionuclide sample container into the assay chamber and raising the radionuclide sample container out of the assay chamber;
   the radionuclide sample lifter comprising:
      a sealed pneumatic system comprising:
         a first stationary shaft and a second stationary shaft, each of the first stationary shaft and the second stationary shaft having a first end and a second end;
         a pneumatic control switch for providing a supply of compressed air to the first end of the first stationary shaft, wherein the pneumatic control switch is connected to the first ends of the first stationary shaft and the second stationary shaft;
         a connecting tube connecting the second ends of the first stationary shaft and the second stationary shaft;
         a magnetically coupled pneumatic actuator comprising an internal magnetic slug provided inside the first stationary shaft and an external magnetic slug provided outside the first stationary shaft, wherein the internal magnetic slug and the external magnetic slug are magnetically coupled so that when the internal magnetic slug moves inside the first stationary shaft, the external magnetic slug also moves with the internal magnetic slug; and
         a sealed passageway for the compressed air comprising the pneumatic control switch, the first and second stationary shafts, and the connecting tube, wherein the sealed passageway prevents the compressed air from being released into the assay chamber;
      wherein the pneumatic control switch providing the supply of compressed air for controlling the movement of the internal magnetic slug and the external magnetic slug;
      a carriage attached to the external magnetic slug, the carriage being configured for holding the radionuclide sample container,
   wherein the magnetically coupled pneumatic actuator moves the carriage between a first position and a second position within the assay chamber,
   wherein the first position places the carriage near the top end of the assay chamber and the second position places the carriage near the bottom end of the assay chamber.

2. The radionuclide dose assay station of claim 1, wherein the movement of the carriage between the first position and the second position is linear.

3. The radionuclide dose assay station of claim 1, wherein the carriage is configured for holding the radionuclide sample container that is a multi-dose vial.

4. The radionuclide dose assay station of claim 1, wherein the carriage is configured for holding the radionuclide sample container that is a unit-dose syringe.

5. A radionuclide sample lifter configured for lowering a radionuclide sample container into an assay chamber and raising the radionuclide sample container out of the assay chamber, the radionuclide sample lifter comprising:
   a sealed pneumatic system comprising:
      a first stationary shaft and a second stationary shaft, each of the first stationary shaft and the second stationary shaft having a first end and a second end;
      a pneumatic control switch for providing a supply of compressed air to the first end of the first stationary shaft, wherein the pneumatic control switch is connected to the first ends of the first stationary shaft and the second stationary shaft;
      a connecting tube connecting the second ends of the first stationary shaft and the second stationary shaft;
      a magnetically coupled pneumatic actuator comprising an internal magnetic slug provided inside the first stationary shaft and an external magnetic slug provided outside the first stationary shaft, wherein the internal magnetic slug and the external magnetic slug are magnetically coupled so that when the internal magnetic slug moves inside the first stationary shaft, the external magnetic slug also moves with the internal magnetic slug; and
      a sealed passageway for the compressed air comprising the pneumatic control switch, the first and second stationary shafts, and the connecting tube, wherein the sealed passageway prevents the compressed air from being released into the assay chamber;

wherein the pneumatic control switch providing the supply of compressed air for controlling the movement of the internal magnetic slug and the external magnetic slug;

a carriage attached to the external magnetic slug, the carriage being configured for holding the radionuclide sample container, wherein the magnetically coupled pneumatic actuator moves the carriage between a first position and a second position within the assay chamber, wherein the first position places the carriage near the top end of the assay chamber and the second position places the carriage near the bottom end of the assay chamber.

6. The radionuclide sample lifter of claim 5, wherein the movement of the carriage between the first position and the second position is linear.

7. The radionuclide sample lifter of claim 5, wherein the carriage is configured for holding the radionuclide sample container that is a multi-dose vial.

8. The radionuclide sample lifter of claim 5, wherein the carriage is configured for holding the radionuclide sample container that is a unit-dose syringe.

9. The radionuclide dose assay station of claim 1, wherein the pneumatic control switch supplies the compressed air through the first end of the first stationary shaft or the first end of the second stationary shaft depending on the intended direction of the movement of the internal magnetic slug inside the first stationary shaft.

10. The radionuclide sample lifter of claim 5, wherein the pneumatic control switch supplies the compressed air through the first end of the first stationary shaft or the first end of the second stationary shaft depending on the intended direction of the movement of the internal magnetic slug inside the first stationary shaft.

* * * * *